(12) United States Patent
Vidal

(10) Patent No.: US 8,461,369 B2
(45) Date of Patent: Jun. 11, 2013

(54) PREPARATION OF ORGANOMONOALKOXY (OR MONOHYDROXY) SILANES FROM ALKOXYSILANES/ORGANOMETALLIC COMPOUNDS

(75) Inventor: Thierry Vidal, Lyons (FR)

(73) Assignee: Rhodia Operations, Aubervilliers (FR)

( * ) Notice: Subject to any disclaimer, the term of this patent is extended or adjusted under 35 U.S.C. 154(b) by 577 days.

(21) Appl. No.: 12/530,005

(22) PCT Filed: Mar. 5, 2008

(86) PCT No.: PCT/EP2008/052671
§ 371 (c)(1),
(2), (4) Date: Mar. 18, 2010

(87) PCT Pub. No.: WO2008/110490
PCT Pub. Date: Sep. 18, 2008

(65) Prior Publication Data
US 2010/0185005 A1    Jul. 22, 2010

(30) Foreign Application Priority Data
Mar. 8, 2007 (FR) .................................... 07 01706

(51) Int. Cl.
*C07F 7/00* (2006.01)
(52) U.S. Cl.
USPC .......................................... 556/466; 556/478
(58) Field of Classification Search
USPC ................................................ 556/466, 478
See application file for complete search history.

(56) References Cited

U.S. PATENT DOCUMENTS

2005/0070731 A1*   3/2005   Guennouni et al. .......... 556/476
2009/0177003 A1    7/2009   Guennouni et al.

FOREIGN PATENT DOCUMENTS

WO    WO 03/027125 A1    4/2003

OTHER PUBLICATIONS

Westermark "On the exchange of ethoxy groups in methylethoxy-silanes for alkyl groups", Department of Organic Chemistry, 1952, pp. 283-284, vol. 64, University of Lund, Lund Sweden, XP009091261.

* cited by examiner

*Primary Examiner* — Porfirio Nazario Gonzalez
(74) *Attorney, Agent, or Firm* — Dentons US LLP

(57) ABSTRACT

Organomonoalkoxy/monohydroxy silanes, particularly halogenated or aklenylated organomonoalkoxy (or monohydroxy) silanes, which are useful intermediates in organic syntheses, are prepared by reacting an alkoxysilane with an organometallic compound suited for substituting at least certain of the alkoxy functions of the alkoxysilane with a monovalent hydrocarbon radical other than alkoxy and co-preparing a metallic alkoxylate by-product capable of denaturing the substituted silanes thus obtained, including contacting the metallic alkoxylate with at least one agent (A) reactive with the alkoxy functions of the alkoxylate to generate one or more species inert relative to the alkoxysilane, such agent (A) being selected from among the electrophile and/or mineral acid groups.

17 Claims, No Drawings

PREPARATION OF ORGANOMONOALKOXY (OR MONOHYDROXY) SILANES FROM ALKOXYSILANES/ORGANOMETALLIC COMPOUNDS

CROSS-REFERENCE TO PRIORITY/PCT APPLICATIONS

This application is a national phase of PCT/EP 2008/052671, filed Mar. 5, 2008 and designating the United States (published in the French language on Sep. 18, 2008, as WO 2008/110490 A1; the title and abstract were also published in English), and claims priority under 35 U.S.C. §119 of FR 0701706, filed Mar. 8, 2007, each hereby expressly incorporated by reference in its entirety and each assigned to the assignee hereof.

The present invention relates to treatments for replacing alkoxy functional groups carried by alkoxysilanes with groups other than alkoxy groups, for example alkyl (in particular methyl) groups or functional groups, such as haloalkyl (in particular halopropyl) groups. These treatments are carried out using optionally halogenated organometallic compounds.

Such replacements are central to certain methods for the synthesis of functionalized, in particular halogenated or alkenylated, organomonoalkoxy (or monohydroxy) silanes and to the use of these organomonoalkoxy (or monohydroxy) silanes as synthetic intermediates in organic chemistry in the production of organomonoalkoxy (or monohydroxy) silanes functionalized by groups other than halogens or alkenyls, for example by amine, thiol or polysulfide groups. The invention is also targeted at the compositions comprising such synthetic intermediates in organic chemistry.

The technical problem at the basis of the invention is related to the fact that the reaction for the substitution of alkoxysilanes by groups other than alkoxy groups generates harmful coproducts, namely metal alkoxides, which are optionally halogenated. These coproducts are harmful because they can be aggressive or denaturing with regard to the substituted alkoxysilanes which it is desired to obtain. In addition, these are coproducts which can complicate the separation and the collection of the products of interest. Finally, they can be waste products which cannot be recovered in value and which are difficult to manage environmentally.

In the particular context of the preparation of functionalized, in particular halogenated or alkenylated, organomonoalkoxy (or monohydroxy) silanes, another technical problem at the root of the invention is that of finding an alternative to the known techniques for the synthesis of functionalized organomonoalkoxy (or monohydroxy) silanes which can make it possible to improve them, for example from the viewpoint of the neutralization of harmful coproducts (of the type of those mentioned above), of the yield, of the productive output, of the cost and of respect for the environment.

Application WO-A-03/027125 describes, inter alia, a process for obtaining functionalized, in particular halogenated, organomonoalkoxysilanes which can be used in particular as synthetic intermediates. This process consists in reacting a halogenated organotrialkoxysilane with an organomagnesium halide compound, so as to obtain the targeted halogenated organomonoalkoxysilane and organomagnesium halide salts, according to the following reaction (Ra):

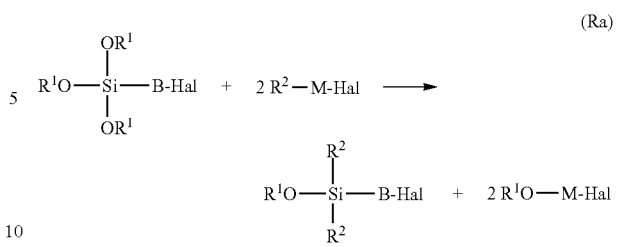

in which, for example:
the symbol $R^1$ is an ethyl group,
B is a divalent residue of formula —$(CH_2)_3$—,
the symbol Hal represents a chlorine atom,
the symbols $R^2$, which are identical or different, each represent a —$CH_3$ group,
the symbol M represents magnesium.

This gives, for example for $R^1$=$CH_3CH_2$—, $R^2$=$CH_3$—, Hal=Cl, B=$CH_2$—$CH_2$—$CH_2$, the following reaction scheme (Ra.1):

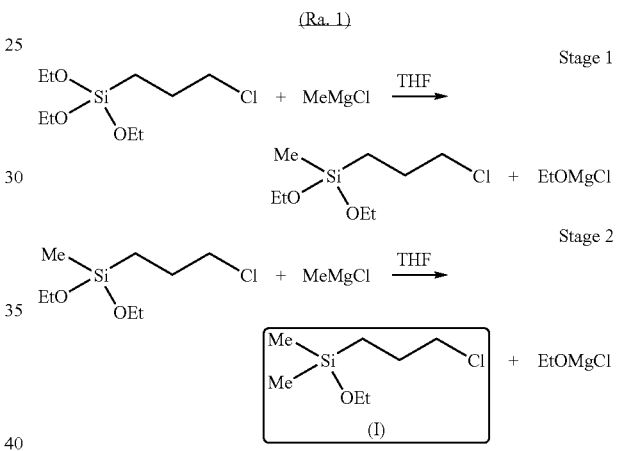

In the end, there is thus present:

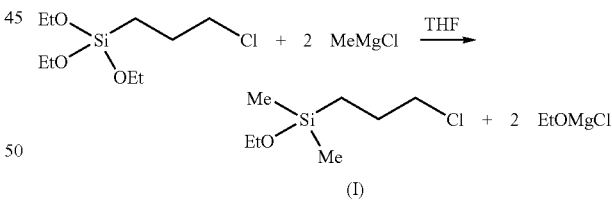

In these reaction schemes, Me and Et respectively symbolize $CH_3$— and $CH_3CH_2$—.

The dimethylethoxy(chloropropyl)silane compound (I) is the intermediate compound targeted. The reaction must thus be halted at this stage if it is desired to optimize the yield. Furthermore, as explained above, the magnesium ethoxides generated during the synthesis of organomonoalkoxysilanes by reaction of alkylmagnesium compounds with alkoxysilanes are undesirable coproducts. They are basic salts which can bring about the decomposition of the silanes formed, in this case the dimethylethoxy(chloropropyl)silane compound (I) targeted in the reactions Ra and Ra.1 described above.

One of the objectives of the present invention is to provide a novel treatment process for the replacement of alkoxy functional groups of alkoxysilanes by groups other than alkoxy groups using at least one organometallic compound, in which the problem of the presence of undesirable coproducts of metal alkoxide type would be solved.

Another objective of the present invention is to provide an alternative to the synthesis of functionalized organomonoalkoxy (or monohydroxy) silanes, in particular halogenated organomonoalkoxy (or monohydroxy) silanes (for example dimethylethoxy(chloropropyl)silane) or alkenylated organomonoalkoxy (or monohydroxy) silanes (for example dimethylethoxyallylsilane), of use in particular as synthetic intermediates in organic chemistry which can make it possible to improve them, for example from the viewpoint of the neutralization of harmful coproducts, of the yield, of the productive output, of the cost, of the compatibility with regard to the environment and/or of the availability of the consumable reactants used.

Another objective of the invention is to provide a process for the preparation of functionalized, in particular halogenated or alkenylated, organomonoalkoxy (or monohydroxy) silanes capable of reacting with a nucleophilic agent in order to produce organomonoalkoxy (or monohydroxy) silanes functionalized, for example, by amine, thiol or polysulfide groups.

Another objective of the invention is also to provide for the use of compounds obtained by this process as intermediates in the synthesis of organomonoalkoxy (or monohydroxy) silanes functionalized, for example, by amine, thiol or polysulfide groups.

These objectives, among others, are achieved by the present invention, which relates first of all to a process for the treatment of at least one alkoxysilane carrying alkoxy functional group(s) of formula OR, in which the R radical is a monovalent hydrocarbon radical, using at least one organometallic compound of formula R'M in which the R' radical is a monovalent hydrocarbon radical other than an alkoxy and M is an alkali or alkaline earth metal, R'M being optionally bonded to at least one halogen X in the case where the valency of M is greater than 1: R'M(X)$_x$ with x=v−1 (v being the valency of M), R'M being in addition capable of replacing at least a portion of the —OR functional groups of the alkoxysilane with the R' radical, which generates a coproduct comprising at least one metal alkoxide of formula MOR in which R and M are as defined above, MOR being optionally bonded to at least one halogen X in the case where the valency of M is greater than 1: (X)$_x$MOR with x=v−1 (v being the valency of M).

This process consists essentially in bringing the metal alkoxide MOR into contact with at least one agent (A) capable of reacting with the alkoxy functional groups OR of this alkoxide MOR in order to generate one or more entities which are inert with regard to the alkoxysilane, said agent (A) being chosen from the group of the electrophiles and/or inorganic acids.

It is to the credit of the inventors to have found a simple, economical, elegant and effective means for converting the coproducts (that is to say, the optionally halogenated metal alkoxides) into chemical entities which, on the one hand, are compatible with the targeted products and which, on the other hand, can easily be managed in terms of treatment, indeed even of recovery in value, of the waste products.

This way of rendering the metal (for example magnesium) alkoxides (for example ethoxides) inert is advantageous in particular in the context of the synthesis of organomonoalkoxysilanes, which consists in reacting alkoxysilanes with organometallic compounds.

The agent (A), which is electrophilic and/or acid, is, for example:
 a derivative of halo(in particular chloro) silane type, in order to generate a metal (in particular magnesium) halide (in particular chloride) and secondarily another alkoxysilane,
 an acyl halide (for example chloride),
 or an inorganic acid, such as HCl or $H_2SO_4$.

The metal (for example magnesium) halide (for example chloride) is an inert entity, that is to say more neutral lato sensu than an alkoxide (for example ethoxide), and can thus make possible the distillation of the noble entities without significant decomposition. In addition, this inert or neutral entity, namely, for example, the magnesium salt, can be directly dissolved in water and can be discharged as aqueous waste since it does not comprise an organic charge (absence of COD).

Furthermore, the alkoxysilane generated in the case where the agent (A) is a silane can be reintroduced as starting reactant in a subsequent metal (for example magnesium) condensation operation. This treatment makes possible satisfactory recovery in value of the ethanol formally generated by this approach for the synthesis of organomonoalkoxysilanes, assuming that the alkoxy substituents are ethoxy substituents.

In its application in the preparation of functionalized, in particular halogenated or alkenylated, organomonoalkoxy (or monohydroxy) silanes (I), the process according to the invention makes possible an improvement in the yields. It is thus possible to recover the organomonoalkoxysilane (I) by distillation in an effective, simple, economical, industrial and selective manner without a problem of management of the effluents, since the metal salts (which can, for example, be magnesium salts) generated are inorganic and can be dissolved in water.

Advantageously, the agent (A) is chosen from the group consisting of the compounds of formula:

in which:
 x1=1, 2 or 3;
 the symbols $X^1$, which are identical to or different from one another, are identical to or different from X and represent a halogen;
 the symbols $Z^1$, which are identical or different, each represent a hydrocarbon radical, preferably a linear, branched or cyclic alkyl radical having from 1 to 8 carbon atoms; an aryl radical having from 6 to 18 carbon atoms; an arylalkyl radical or an alkylaryl radical (C6-C18 aryl, C1-C6 alkyl), $Z^1$ optionally carrying at least one halogenated or perhalogenated group;

in which:
 the symbols $X^2$ are identical to or different from one another and correspond to the same definition as $X^1$;
 the symbols $Z^2$ are identical to or different from one another and correspond to the same definition as $Z^1$;
 (A.c):

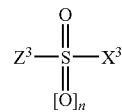

in which:

n=0 or 1;
the symbols $X^3$ are identical to or different from one another and correspond to the same definition as $X^1$;
the symbols $Z^3$ are identical to or different from one another and correspond to the same definition as $Z^1$;

(A.d):

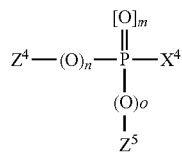

in which:

m, n and o=0 or 1;
the symbols $X^4$ are identical to or different from one another and correspond to the same definition as $X^1$;
the symbols $Z^4$ are identical to or different from one another and correspond to the same definition as $Z^1$;
the symbols $Z^5$ are identical to or different from one another and correspond to the same definition as $Z^1$;
and their mixtures.

It is preferable for $X^1$, $X^2$, $X^3$ and $X^4$ each to be a halogen identical to that which is involved in the reaction between the alkoxysilane and the metal entity M.

A preferred example of the electrophilic agent (A.a) is chloropropyltrichlorosilane.

A preferred example of the electrophilic agent (A.b) is chloroacetate.

A preferred example of the electrophilic agent (A.c) is mesyl chloride.

A preferred example of the electrophilic agent (A.d) is diethyl chlorophosphate.

According to an advantageous form of the invention, the agent (A) is introduced into the reaction medium at least in part before and/or during and/or after, preferably after, the appearance of the alkoxide coproduct $(X)_x MOR$ in this reaction medium.

Preferably, the metal M is chosen from the group consisting of Mg, Na, Li, Ca, Ba, Cd, Zn, Cu, their mixtures and their alloys, magnesium being preferred.

One of the key elements of the "dealkoxylation" treatment process according to the invention is the reaction between the metal alkoxide $(X)_x MOR$ [hereinafter denoted by the reference (IV)] and the agent (A), in particular electrophile.

In the case where the agent (A) is of (A.a) type, this reaction is advantageously as follows:

Reaction 1

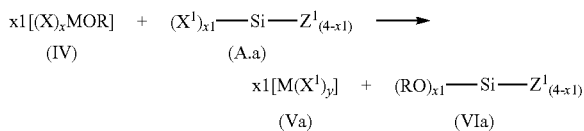

with x1, X, M, R, $X^1$ and $Z^1$ as defined above and y corresponding to the valency v of the metal M.

In the case where the agent (A) is of (A.b) type, the reaction between the metal alkoxide $(X)_x MOR$ [hereinafter denoted by the reference (IV)] and the agent (A.b) is advantageously as follows:

Reaction 2

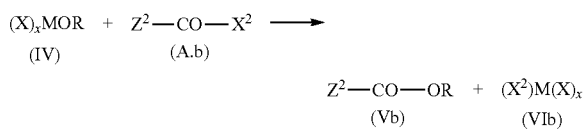

with X, M, R, $Z^2$ and $X^2$ as defined above.

The amounts of agent (A) employed are a consequence of the stoichiometry of the reaction for the inactivation of the alkoxide (IV) (in particular of reactions 1 and 2 targeted above). In practice, they are advantageously 1.2±0.5 times the molar stoichiometry and more preferably still one times the molar stoichiometry.

The operating conditions under which the inactivation of the alkoxide (IV) of the alkoxide coproduct $(X)_x MOR$ by the agent (A) takes place are, for example, a reaction temperature of between 0 and 200° C. and a pressure equal to atmospheric pressure.

As indicated above, the treatment process according to the invention has a particularly advantageous application in the preparation of functionalized organoalkoxy (or hydroxy) silanes, in particular functionalized organomonoalkoxy (or monohydroxy) silanes, which are in particular halogenated or alkenylated.

In particular, these functionalized organomonoalkoxy (or monohydroxy) silanes can correspond to the following formula (I):

in which:

the symbol $R^1$ represents hydrogen or a monovalent hydrocarbon group corresponding to R, $R^1$ being in the latter case chosen from linear, branched or cyclic alkyl radicals having from 1 to 25, preferably from 1 to 8, carbon atoms and linear, branched or cyclic alkoxyalkyl radicals having from 2 to 25, preferably from 2 to 8, carbon atoms;

the symbols $R^2$, which are identical or different, are each a monovalent hydrocarbon group, other than an alkoxy, corresponding to R' and each represent a linear, branched or cyclic alkyl radical having from 1 to 25, preferably from 1 to 8, carbon atoms; an aryl radical having from 6 to 18 carbon atoms; an arylalkyl radical or an alkylaryl radical ($C_6$-$C_{18}$ aryl, $C_1$-$C_6$ alkyl); $R^2$ optionally carrying at least one halogenated or perhalogenated group;

the symbol Y represents either —B—$Y^1$ or $Y^2$:

with $Y^1$ corresponding to:

i.1) a halogen atom (symbol Hal), preferably chosen from chlorine, bromine and iodine atoms;

ii.1) an $R^3$ group corresponding to a linear, branched or cyclic alkyl radical having from 1 to 8 carbon atoms, an aryl radical having from 6 to 18 carbon atoms, an arylalkyl radical or an alkylaryl radical ($C_5$-$C_{18}$ aryl, $C_1$-$C_6$ alkyl), $R^3$ optionally comprising at least one heteroatom and optionally carrying at least one halogenated or perhalogenated group;

iii.1) or a monovalent organic functional group W chosen from the group consisting of linear, branched or cyclic alkoxyl or acyl radicals having from 2 to 8 carbon atoms, amino, mercapto, cyano, thiocyanato, oxycyanato and (organosilyl)organopolythio groups, it being possible for these groups also to be substituents of the alkoxyl or acyl radicals, and the mixtures of these radicals and groups;

with $Y^2$ corresponding to R' and representing a monovalent organic functional group $R^4$ chosen from functional groups comprising at least one ethylenic and/or acetylenic unsaturation, in particular selected from:

linear, branched or cyclic alkenyl groups $R^{4.1}$ having from 2 to 10 carbon atoms, linear, branched or cyclic alkynyl groups $R^{4.2}$ having from 2 to 10 carbon atoms, linear, branched or cyclic -(alkenyl-alkynyl) or -(alkynyl-alkenyl) groups $R^{4.3}$ having from 5 to 20 carbon atoms, the $R^{4.1}$ radicals being preferred, and with B corresponding to a linear, branched or cyclic $C_1$-$C_{10}$ alkylene residue or a divalent aromatic residue chosen from:

(ortho-, meta- or para-)phenylene-(linear or branched $C_2$-$C_6$)alkylene-, (linear or branched $C_2$-$C_6$)alkylene-(ortho-, meta- or para-)phenylene-, and (linear or branched $C_2$-$C_6$)alkylene-(ortho-, meta- or para-)phenylene-(linear or branched $C_2$-$C_6$) alkylene-;

and Y being able in addition optionally to comprise at least one heteroatom and/or to carry one or more aromatic groups.

This preparation process is of the type of those which consist essentially in reacting at least one organometallic reactant, which comprises the metal M and which is optionally generated in situ, with at least one organoalkoxysilane (II) chosen from di-, tri- and tetraalkoxysilanes and their mixtures and of the type of those in which at least one of the coproducts comprises at least one metal alkoxide halide (IV) comprising the metal M.

In accordance with the invention, this preparation process is characterized in that the alkoxysilane carrying alkoxy functional group(s) of formula OR is an organoalkoxysilane (II) chosen from di-, tri- and tetraalkoxysilanes and their mixtures and is brought into contact with the organometallic compound (III) of formula R'M in order to generate the coproduct (IV) comprising at least one metal alkoxide of formula $(X)_x MOR$.

According to a first embodiment, the preparation process is of the type of those which consist essentially in reacting at least one halogenated organoalkoxysilane (II) chosen from di-, tri- and tetraalkoxysilanes and their mixtures with at least one organometallic compound (III) of formula $R^2$-M in the presence of at least one solvent (S1) having a starting boiling point SBP(S1) of less than or equal to the boiling point BP(I) of the organomonoalkoxysilane (I) and optionally of at least one solvent (S2) having a starting boiling point SBP(S2) of greater than or equal to SBP(I), SBP(S1) being less than or equal to SBP(S2), this organometallic compound (III) being capable of replacing the alkoxy radicals by organic radicals, in particular according to the following reaction scheme:

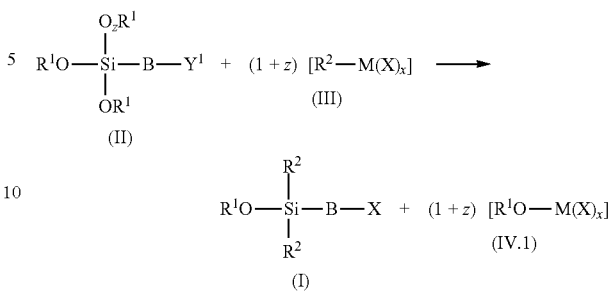

Reaction 3 where z=0 or 1 and the symbols X, x, M, $R^1$, $R^2$ and B are as defined above;

the coproduct (IV.1) being a metal alkoxide halide comprising the metal M.

Advantageously, this process comprises the following stages:

Phase -a-: addition/reaction comprising the following (successive or nonsuccessive) stages:

-a1- addition of a solution of the organometallic compound (III) in a solvent S1 to the compound (II);

-a2- reaction of (II) with (III), resulting in the production of a suspension of the reaction products (I) and (IV) in S1;

-a3- optional addition of a solvent S2 before and/or during and/or after reaction -a2-;

Phase -b-: treatment of the metal alkoxide halide coproduct (IV.1) using the agent (A), in particular electrophile, in order to obtain the coproducts (V.1) and (VI.1);

Phase -c-: removal of S1, preferably by distillation;

Phase -d-:

-d1- dissolution of the coproduct (V.1), which can be a metal salt (Va.1), with water;

-d2- optional removal of the solution obtained in d1;

Phase -e-: separation and collection of the organomonoalkoxysilane (I), preferably by distillation and more preferably still by distillation under reduced pressure; the product (VI.1) of reactions 1 and 2 included in the distillation residue optionally being recycled in reaction 3;

Phase -f-: optional stage of hydrolysis which makes it possible to convert organomonoalkoxysilane (I) into organomonohydroxysilane (I);

it being possible for phases -d- and -e- optionally to be inverted.

According to an advantageous form, it is possible to dilute the reaction medium for the implementation of phase -c-, in order to reduce the concentration of salt (V.1). To do this, it may be appropriate to use the organoalkoxysilane (II) as diluent.

In this first embodiment, preferably, on the one hand, use is made of a heavy solvent, for example of water-immiscible hydrocarbon type, after the reaction of the halometallic compound (III), in which the metal salts (for example magnesium salts) formed are in the powder form and can thus be perfectly stirred (which makes it possible to envisage a distillation) and, on the other hand, the organomonoalkoxysilane (I) is distilled, preferably under reduced pressure.

Phase -d- consists in dissolving the salts formed once the organomonoalkoxysilane (I) has departed from the reaction medium. This makes it possible to avoid the hydrolysis of the organomonoalkoxysilane (I) and to recycle the heavy solvent S2 in the process without treatment.

According to a second embodiment, the preparation process according to the invention is of the type of those which consist essentially in reacting at least one nonhalogenated organoalkoxysilane (II), chosen from di-, tri- and tetraalkoxysilanes and their mixtures, with at least one halogenated organic compound (III) (preferably an allyl halide) in the presence of at least one metal (M) and in the presence of at least one solvent (S1) having a starting boiling point SBP(S1) of less than or equal to the boiling point BP(I) of the organomonoalkoxysilane (I) and optionally of at least one solvent (S2) having a starting boiling point SBP(S2) of greater than or equal to SBP(I), SBP(S1) being less than or equal to SBP(S2), this halogenated organic compound (III) being capable of replacing the alkoxy radicals with organic radicals, according to the following reaction scheme (reaction II/III), which illustrates the specific case where the organoalkoxysilane (II) is a dialkoxysilane:

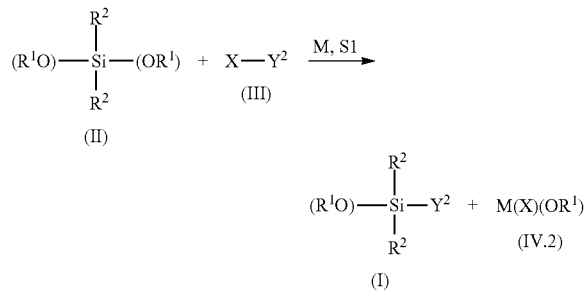

where:
the symbols M, X, $R^1$, $R^2$, B and $Y^2$ are as defined above, the coproduct (IV.2) being a metal alkoxide halide comprising the metal M.

Preferably, the reaction between the metal alkoxide halide comprising the metal M (IV.2) and the agent (A.b), in particular electrophile, is as follows:

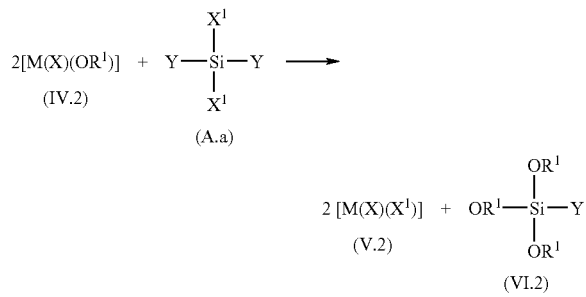

More preferably still, the process according to the second embodiment comprises the following stages:
-a- bringing the metal M and the solvent S1, indeed even optionally a solvent S2, together;
-b- optional activation of the reaction, preferably by addition of a catalytic amount of at least one halogen and/or of an alkyl halide and/or by heating the reaction medium and/or the metal M;
-c- addition of the organoalkoxysilane (II);
-d- addition of the halogenated organic compound (III), gradually and at a rate of introduction into the reaction medium which is less than or equal to the rate of consumption of (III) in reaction (II/III);
-e- reaction (II/III), resulting in the production of the reaction product (I);
the temperature of the reaction medium preferably being maintained at a temperature RT of less than or equal to the boiling point BP(S1) of the solvent S1;
-e1- optional addition of S2;
-f- treatment of the coproduct (IV.2) using the agent (A) in order to obtain the coproducts (V.2) and (VI.2);
-h- separation and collection of the organomonoalkoxysilanes (I) and (VI.2), preferably by distillation and more preferably still by distillation under reduced pressure;
-i- dissolution in water of the coproduct (V.2), which can be a metal salt (Va.2);
-j- optional removal of the solution obtained in -i-;
-k- removal of S1, preferably by distillation;
-l- optional stage of hydrolysis which makes it possible to convert organomonoalkoxysilane (I) into organomonohydroxysilane (I).

According to an advantageous characteristic of the preparation process according to the second embodiment of the invention, during stage -d-, the halogenated organic compound (III) is introduced into the reaction medium in an equivalent molar amount, indeed even in slight excess or in slight deficiency, with respect to the starting alkoxysilane (II). "Slight" deficiency or excess is understood to mean, for example, within the meaning of the invention, a margin of ±5 mol %.

The process according to the second embodiment of the invention can thus make it possible to recover the targeted functionalized (preferably alkenylated) organomonoalkoxy (or monohydroxy) silane in a selective, effective, simple, direct, economical and industrial fashion without too many constraints in terms of ecotoxicity (treatment of the effluents). The coproducts, such as the metal salts (for example magnesium salts), are formed in smaller amounts in comparison with those observed in the known routes, in particular the Grignard route. The process according to the invention is advantageously "ecocompatible".

This process consists, inter alia, in slowly introducing the compound (III), for example the allyl halide, onto a heel comprising the organoalkoxysilane silicon derivative (II) and the metal (M), in particular magnesium, for example in the form of turnings.

For example, the molar ratios of these reactants (III), (II) and metal (M), in particular magnesium, are stoichiometric. It is also possible to use an excess of metal (in particular magnesium) in order to limit further still the formation of bisallyl.

According to an alternative form of the second embodiment, the optional addition of S2 to the reaction medium, at the start of the process, for example with S1, in particular during stage -a-, and/or during the optional stage -e1-, is advantageously associated not only with a stage -h- of separation and collection of a functionalized organomonoalkoxy (or monohydroxy) silane (I), preferably by distillation and more preferably still by distillation under reduced pressure, but also with stage -i-, which occurs, advantageously, after stage -h- and which consists in dissolving the metal salts (for example magnesium salts) present in the solid form (for example in suspension) in the reaction medium, this dissolution preferably being carried out by addition of an acidic aqueous solution. The metal salts (for example magnesium salts) thus dissolved form coproducts which are relatively easy to manage environmentally.

It is possible to envisage, in accordance with the second embodiment, for the optional addition of S2 to take place not only during stage -a- and/or during the optional stage -e1- but also at any point of the process, preferably before and/or during stage -h-, on at least one occasion.

Quantitatively, in general, the solvent S1 is employed in such a way that the S1/M molar ratio is between 3:1 and 1:1, preferably between 2.5:1 and 1.5:1 and more preferably still equal to approximately 2:1.

It is generally preferable for the temperature of the reaction medium RT to be between approximately (BP(S1)−(BP(S1)× 0.50)) and BP(S1), in particular between approximately (BP (S1)−(BP(S1)×0.20)) and BP(S1).

Examples of temperature ranges for RT according to the nature of the solvent S1 are given below without implied limitation:

Diethyl ether: 30° C.≦RT≦40° C.
THF: 30° C.≦RT≦65° C.

Preferably, in this second embodiment, the halogenated organic compound (III) is a haloalkenyl, preferably an allyl or methallyl, isopenyl, butenyl or hexenyl, which may or may not be cyclic, halide (in particular chloride or bromide) and more preferably still an allyl chloride or bromide.

According to a particularly advantageous characteristic of this second embodiment, stage -h- of separation and of collection of the compound (I) is carried out batchwise on at least one occasion, preferably by distillation under reduced pressure.

In order to complete the performance of this second embodiment of the process of the invention, in particular with regard to selectivity, it is advantageous to use an M/(II) molar ratio of between 1.4:1 and 1:1, preferably between 1.3:1 and 1.1:1 and more preferably still equal to approximately 1.2:1.

In the first and second embodiments of the invention described above, the boiling point "BP" of a compound corresponds to its starting boiling point, according to the ASTM D 86-99 standardized test.

In order to facilitate the separation of the products (I) targeted in the preparation process according to the invention and in the case where the agent (A) is of (A.b) type, the $Z^2$ radical of the agent (A.b) is chosen so that the product (Vb) of reaction 2 has a starting boiling point SBP(Vb) which exhibits, with respect to SBP(S2) and/or with respect to SBP(I), a difference of at least 5° C., preferably of at least 10° C., more preferably of at least 30° C. and more preferably still of at least 40° C.

Preferably, S1 is chosen from the group of the ethereal organic compounds and/or from the group of the acetals and in particular from the subgroup consisting of tetrahydrofuran (THF), methyl-THF (Me-THF), dialkyl ethers (preferably dibutyl ether), dioxanes and their mixtures.

Preferably, S2 is chosen from the group of the compounds having a starting boiling point SBP defined as follows: 150° C. 5 SBP, preferably 180° C.≦SBP and more preferably still 190° C.≦SBP≦350° C.

S2 is generally chosen from the group of the compounds consisting of silanes (in particular alkoxysilanes), hydrocarbons, hydrocarbon fractions, (poly)aromatic compounds (in particular alkylbenzenes), alkanes (in particular heavy alkanes), (poly)ethers, phosphorus-comprising compounds, sulfolanes (in particular dialkyl sulfones), ionic liquids, dialkylnitriles and their mixtures.

Mention may be made, as examples of commercial products capable of being used as solvent S2, of petroleum fractions or hydrocarbon fractions, in particular those sold under the name Isopar® M, N or P by Exxon Mobil Chemical.

Advantageously, the amount of solvent S2 in the reaction medium can be between 50 and 300 g per 300 g of reaction medium, before stage -a4- of removal of S1, preferably by distillation.

The amount of solvent S1 and/or S2 is generally set so that the reaction medium can be stirred.

In accordance with the invention, the incorporation of S2 in the reaction medium is carried out, preferably, as soon as the organic compound (II) is consumed to a level of at least 70% by weight, preferably at least 90% by weight, by the reaction of (II) with (III).

As regards the products employed, they can in practice be, for example, those in which:
the $R^1$ radicals are chosen from the following radicals: methyl, ethyl, n-propyl, isopropyl, n-butyl, $CH_3OCH_2$—, $CH_3OCH_2CH_2$— and $CH_3OCH(CH_3)CH_2$—,
the $R^2$ radicals are chosen from the following radicals: methyl, ethyl, n-propyl, isopropyl, n-butyl, n-hexyl and phenyl,
the $Y^2$ radical represents:

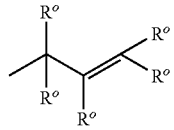

the symbol $R^o$ representing radicals which are identical to or different from one another and which correspond to hydrogen or to a linear, branched or cyclic alkyl having from 1 to 8 carbon atoms, preferably —$CH_3$ or —$CH_2CH_3$.

Preferably, in the functionalized, in particular halogenated, organomonoalkoxysilanes corresponding to the formula (I), the B radical can represent an alkylene which corresponds to the following formulae:

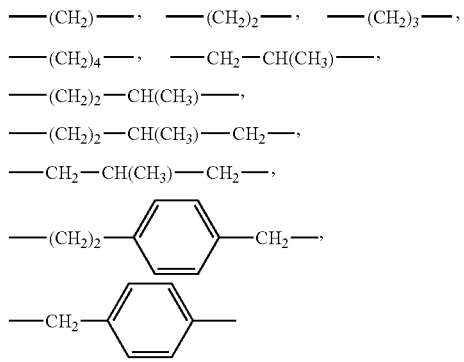

In accordance with a preferred embodiment of the invention, at least one of the following definitions is complied with:
the symbols $R^1$ and $R^2$, which are identical or different, each represent $CH_3CH_2$— or $CH_3$— (preferably, $R^1$ represents $CH_3CH_2$— and $R^2$ represents $CH_3$—);
the symbol M represents Mg;
the symbol B represents —$(CH_2)_3$—;
the symbol Y corresponds to Hal, which itself advantageously represents Cl;
in the formulae given in the present account.

In practice, the reaction pressure is, for example, ambient atmospheric pressure.

The process according to the invention can comprise continuous sequences. It is preferably semicontinuous.

The process according to the invention applies, for example, to the preparation of organomonoalkoxysilanes (I) with the formulae:

first embodiment (halogenated organomonoalkoxysilanes):

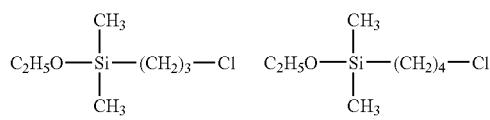

second embodiment (alkenylated organomonoalkoxysilanes):

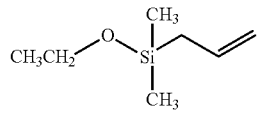

The invention also relates to the use of an organomonoalkoxysilane of formula:

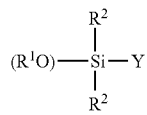
(I)

obtained (directly) by the process described above, in the presence
of least one electrophilic agent (A) of formula:

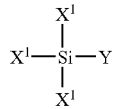
(A.a)

and/or of at least one coproduct of formula:

x1[M(X$^1$)$_y$]  (Va)

and/or of at least one coproduct of formula:

Z$^2$—CO—OR  (Vb)

in which formulae R$^1$, R$^2$, Y, X$^1$, x1, Z$^2$ and R are as defined above,
as intermediate in the synthesis of organomonoalkoxy (or monohydroxy) silanes functionalized, for example, by amine, thiol or polysulfide groups.

In this use, the symbols R$^1$ and R$^2$, which are identical or different, preferably each represent CH$_3$CH$_2$— or CH$_3$— (preferably, R$^1$ represents CH$_3$CH$_2$— and R$^2$ represents CH$_3$—), the symbol M represents Mg and the symbol X$^1$ represents Cl.

In accordance with the invention, the product (I):

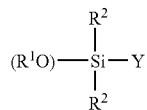
(I)

obtained on conclusion of the process according to the invention is a synthetic intermediate capable of reacting with at least one nucleophilic agent for the production of functionalized organosilanes of formula (VIII):

(VIII)

R$^1$, R$^2$, B, Y and W of the formulae (I) and (VIII) are as defined above.

The nucleophilic agent with which the synthetic intermediate (I) is capable of reacting for the production of functionalized organosilanes of formula (VIII) can be of different natures. In particular, the nucleophilic agent may, for example, relate to the nucleophilic agents as described on page 12, line 10 to page 14, line 27 of application WO-A-03/027125.

As regards the practical way of carrying out the abovementioned synthesis, reference may be made for further details to the content, for example, of EP-A-0 848 006, which illustrates, starting from other reactants, procedures which can be applied in carrying out the synthesis under consideration.

The examples which follow illustrate the present invention without limiting the scope thereof.

EXAMPLES

First Embodiment

Magnesium Route

| FORMULAE | PRODUCTS USED |
|---|---|
| (R$^1$O)—Si(R$^2$)(R$^2$)—Y<br>(I) | C$_2$H$_5$O—Si(CH$_3$)(CH$_3$)—(CH$_2$)$_3$—Cl |
| R$^1$O—Si(OR$^1$)(OR$^1$)—B—Y$^1$<br>(II) | CH$_3$CH$_2$O—Si(OCH$_2$CH$_3$)(OCH$_2$CH$_3$)—(CH$_2$)$_3$—Cl |
| (R$^2$—M-Hal)<br>(III)<br>(1 + z) (R$^1$O—M-Hal)<br>(IV.1) | CH$_3$MgCl<br><br>CH$_3$CH$_2$OMgCl |
| X$^1$—Si(X$^1$)(X$^1$)—Y<br>(A.a) | Cl—Si(Cl)(Cl)—CH$_2$CH$_2$CH$_2$—Cl<br>(A.a) |
| S1<br>S2 | THF<br>ISOPAR M |

Block Diagram

```
(II) ──────────►
(III) in S1 ───► [Reaction]

(A.a) ────────► [Treatment of (IV.1)]

(II) ─────────► [Distillation S1] ────► S1

H₂O ──────────► [Hydrolysis] ─────────► Mg salts

[Distillation (I) and (II)] ────► (I)

(II) to be recycled
```

Equation of the Chemical Balances

Stage 1
$(EtO)_3Si$–(CH₂)₃–Cl + 2 MeMgCl ⟶
(II)                    (III)

$\begin{array}{c}Me\\ \phantom{x}\diagdown\\ Si\\ EtO\diagup\phantom{x}\diagdown Me\end{array}$–(CH₂)₃–Cl + 2 EtOMgCl
(I)                                    (IV.1)

Stage 2
2/3 Cl₃Si–(CH₂)₃–Cl + 2 EtOMgCl ⟶
    (A.a)              (IV.1)

2/3 (EtO)₃Si–(CH₂)₃–Cl + 2 MgCl₂
    (II)                  (V.1)

1/3 (II) + 2/3 (A.a) + 2 (III) ⟶ (I) + 2 (V.1)

Overall balance

Preparation of 3-chloropropylethoxydimethylsilane (I)

Example 1

Isolation without Treatment of the Magnesium Salts

In a Jacketed Reactor:
Phase -a-:
3-chloropropyltriethoxysilane (II) (76.4 g, 0.3 mol) is charged at 15-25° C.
-a1- heating is carried out at 70° C. and methylmagnesium chloride (22% solution in THF (S1), 225 g; 0.66 mol) is added with stirring over approximately 1 h
-a2- the mixture is kept stirred at 70° C. for 3 hours
-a3- Isopar M (S2) (245 g) is added at a temperature of between 30 and 180° C.
-a4- the THF is distilled under 100 mbar at a temperature of between 50 and 100° C.
Phase -b-:
3-chloropropylethoxydimethylsilane (I) is distilled. The fraction obtained (92.0 g) comprises 16% of 3-chloropropylethoxydimethylsilane (14.7 g; isolated yield of 27%) and impurities.

Example 2

Isolation with Treatment of the Magnesium Salts and Recovery in Value of the Silane Formed In a Jacketed Reactor:
Phase -a-:
3-chloropropyltriethoxysilane (II) (76 g, 0.3 mol) is charged at 15-25° C.
-a1- heating is carried out at 70° C. and methylmagnesium chloride (22% solution in THF (S1), 225 g; 0.66 mol) is added with stirring for approximately 1 h
-a2- the mixture is kept stirred at 70° C. for 3 hours
Phase -b-:
3-chloropropyltrichlorosilane (A.a) (45 g) is added at a temperature of between 30 and 180° C.
Phase -c-:
3-chloropropyltriethoxysilane (II, S2) (150 g) is charged at 15-25° C.
the THF is distilled under 100 mbar at a temperature of between 50 and 100° C.
Phase -d-:
the reaction medium is run onto water
the saline aqueous phase is separated by settling
Phase -e-:
3-chloropropylethoxydimethylsilane (I) is distilled. The fraction obtained (50.0 g) comprises 96% of 3-chloropropylethoxydimethylsilane (48 g; isolated yield of 88%)
the 3-chloropropyltriethoxysilane remaining in the reactor is collected.

Example 3

Isolation with Treatment of the Magnesium Salts in Order to Render the Reaction Medium Easier to Separate In a Jacketed Reactor:
Phase -a-:
3-chloropropyltriethoxysilane (II) (76 g, 0.3 mol) is charged at 15-25° C.
-a1- heating is carried out at 70° C. and methylmagnesium chloride (22% solution in THF (S1), 225 g; 0.66 mol) is added with stirring for approximately 1 hour
-a2- the mixture is kept stirred at 70° C. for 3 hours
Phase -b-:
acetyl chloride (A.b) (47 g) is added at a temperature of between 30 and 180° C.
Phase -c-:
Isopar M (S2) (200 g) is charged at 15-25° C.
the THF and the ethyl acetate (A.b) formed are distilled under 100 mbar at a temperature of between 50 and 100° C.
Phase -d-:
the reaction medium is run onto water
the saline aqueous phase is separated by settling Phase -e-:
3-chloropropylethoxydimethylsilane (I) is distilled. The fraction obtained (49.5 g) comprises 96.5% of 3-chloropropylethoxydimethylsilane (47.7 g; isolated yield of 88%)
the Isopar M remaining in the reactor is collected.

Second Embodiment

Barbier Route

Equation of the Chemical Balances

Stage 1

$$\text{AC} \quad \diagup\!\!\!\diagdown\!\!\!\diagdown\text{Cl} + \text{Mg} + \text{Me}_2\text{Si(OEt)}_2 \longrightarrow$$
(II)

$$\underset{\text{EtO}}{\overset{\text{Me}}{\diagdown}}\text{Si}\underset{\text{Me}}{\diagdown}\diagup\!\!\!\diagdown + \text{EtOMgCl}$$
(I)                                      (III)

Stage 2

1/2 Me$_2$SiCl$_2$ + EtOMgCl $\longrightarrow$ 1/2 Me$_2$Si(OEt)$_2$ + MgCl$_2$
     (A.a)            (III)                           (II)          (V.1)

AC + 1/2 (II) + 1/2 (A.a) + Mg $\longrightarrow$ (I) + (V.1)

Overall balance

Preparation of Dimethylethoxyallylsilane

Example 4

Isolation with Treatment of the Magnesium Salts and Recovery in Value of the Silane Formed In a Jacketed Reactor:
a—magnesium (M) (35 g, 1.44 mol) is charged at 15-25° C., followed by dibutyl ether (200 g) and a solution of iodine in dibutyl ether (0.07 g in 5 g)
b—heating is carried out to 130° C. and this temperature is maintained until the reaction medium has decolored
c—dimethyldiethoxysilane (140 g, 0.94 mol) is added at 130° C.
d—allyl chloride in solution in dibutyl ether is run in at 130° C. (88 g in 212 g)
e—the temperature of the reaction medium is maintained at 120-130° C. for 5 hours
f—dimethyldichlorosilane (A.a) (66.7 g, 0.47 mol) is added at 120-130° C.
g—the reaction medium is cooled to 15-20° C.
h—the reaction medium is run onto a water heel (320 g)
i—the saline aqueous phase is separated by settling and collected
j—dimethyldiethoxysilane (62 g) and dimethylethoxyallylsilane (118 g) are finely distilled under vacuum (400 mbar)
k—the dibutyl ether is collected.

Example 5

Isolation with Treatment of the Magnesium Salts in Order to Render the Reaction Medium Easier to Separate In a Jacketed Reactor:
a—magnesium (II) (35 g, 1.44 mol) is charged at 15-25° C., followed by dibutyl ether (200 g) and a solution of iodine in dibutyl ether (0.07 g in 5 g)
b—heating is carried out to 130° C. and this temperature is maintained until the reaction medium has decolored
c—dimethyldiethoxysilane (140 g, 0.94 mol) is added at 130° C.
d—allyl chloride in solution in dibutyl ether is run in at 130° C. (88 g in 212 g)
e—the temperature of the reaction medium is maintained at 120-130° C. for 5 hours
f—acetyl chloride (A.b) (74 g, 0.94 mol) is added at 120-130° C.
g—the ethyl acetate generated is distilled at atmospheric pressure
h—the reaction medium is cooled to 15-20° C.
i—the reaction medium is run onto a water heel (320 g)
j—the saline aqueous phase is separated by settling and collected
k—dimethylethoxyallylsilane (116 g) is distilled under vacuum (400 mbar)
l—the dibutyl ether is collected.

The invention claimed is:

1. A process for the preparation of an organomonoalkoxy/monohydroxy silane, comprising reacting an alkoxysilane with an organometallic compound suited for substituting at least certain of the alkoxy functions of said alkoxysilane with a monovalent hydrocarbon radical other than alkoxy and co-preparing a metallic alkoxylate by-product capable of denaturing the substituted silanes thus obtained, including contacting said metallic alkoxylate with at least one agent (A) reactive with the alkoxy functions of the said alkoxylate to generate one or more species inert relative to the alkoxysilane, said agent (A) being selected from among the electrophile and/or mineral acid groups.

2. The process as defined by claim 1, further comprising preparing at least one halogenated or alkenylated organomonoalkoxy or organomonohydroxy silane.

3. A process for the preparation of an organomonoalkoxy/monohydroxy silane, comprising reacting in a reaction medium at least one alkoxysilane bearing alkoxy functional group(s) of the formula OR, in which R is a monovalent hydrocarbon radical, with at least one organometallic compound of formula R'M, in which R' is a monovalent hydrocarbon radical other than alkoxy and M is an alkali or alkaline earth metal, wherein R'M is optionally bonded to at least one halogen X in the event that the valency of M is greater than 1, said organometallic compound R'M being suited for substituting at least certain of the —OR functional groups of said alkoxysilane with the —R' radical and co-preparing at least one metallic alkoxylate by-product of formula MOR, in which M and R are as defined above, MOR being optionally bonded to at least one halogen X in the event that the valency of M is greater than 1, including contacting said metallic alkoxide MOR with at least one agent (A) reactive with the alkoxy functional groups —OR of said alkoxide MOR to generate one or more species which are inert with respect to the alkoxysilane, said agent (A) being selected from among the electrophiles and/or mineral acids.

4. The process as defined by claim 3, wherein the at least one agent (A) is selected from the group consisting of the compounds of formula:

$$(X^1)_{x1}—Si—Z^1_{(4-x1)} \quad (A.a):$$

in which:

x1=1, 2 or 3;

the symbols $X^1$, which may be identical or different, are identical to or different from X and are each a halogen atom;

the symbols $Z^1$, which may be identical or different, are each a linear, branched or cyclic alkyl radical having from 1 to 8 carbon atoms, an aryl radical having from 6 to 18 carbon atoms, an arylalkyl radical or an alkylaryl radical (C6-C18 aryl, C1-C6 alkyl), $Z^1$ optionally bearing at least one halogenated or perhalogenated substituent;

$$Z^2—CO—X^2 \quad (A.b):$$

in which:

the symbols $X^2$, which may be identical or different, have the same definition as $X^1$;

the symbols $Z^2$, which may be identical or different, have the same definition as $Z^1$;

(A.c):

$$Z^3—\underset{[O]_n}{\overset{O}{\underset{\|}{\overset{\|}{S}}}}—X^3$$

in which:

n=0 or 1;

the symbols $X^3$, which may be identical or different, have the same definition as $X^1$;

the symbols $Z^3$, which may be identical or different, have the same definition as $Z^1$;

(A.d):

$$Z^4—(O)_n—\underset{\underset{Z^5}{\overset{|}{(O)_o}}}{\overset{[O]_m}{\overset{\|}{P}}}—X^4$$

in which:

m, n and o=0 or 1;

the symbols $X^4$, which may be identical or different, have the same definition as $X^1$;

the symbols $Z^4$, which may be identical or different, have the same definition as $Z^1$;

the symbols $Z^5$, which may be identical or different, have the same definition as $Z^1$; and mixtures thereof.

5. The process as defined by claim 3, wherein the at least one agent (A) is introduced into the reaction medium at least in part before and/or during and/or after the appearance of the alkoxide by-product $(X)_xMOR$ in said reaction medium.

6. The process as defined by claim 3, wherein the metal M is selected from the group consisting of Mg, Na, Li, Ca, Ba, Cd, Zn, Cu, and the mixtures and alloys thereof.

7. The process as defined by claim 4, wherein the reaction between the metal alkoxide $(X)_xMOR$ and the agent (A.a) is as follows:

Reaction 1

$$x1[(X)_xMOR] + (X^1)_{x1}—Si—Z^1_{(4-x1)} \longrightarrow$$
$$(IV) \qquad\qquad (A.a)$$
$$x1[M(X^1)_y] + (RO)_{x1}—Si—Z^1_{(4-x1)}$$
$$(Va) \qquad\qquad (VIa)$$

wherein y is the valency v of the metal M.

8. The process as defined by claim 4, wherein the reaction between the metal alkoxide $(X)_xMOR$ and the agent (A.b) is as follows:

Reaction 2

$$(X)_xMOR + Z^2—CO—X^2 \longrightarrow$$
$$(IV) \qquad (A.b)$$
$$Z^2—CO—OR + (X^2)M(X)_x.$$
$$(Vb) \qquad\qquad (VIb)$$

9. The process as defined by claim 3, further comprising preparing functionalized organoalkoxy (or hydroxy) silanes which may be halogenated or alkenylated, of formula (I)

$$(R^1O)—\underset{R^2}{\overset{R^2}{\underset{|}{\overset{|}{Si}}}}—Y \quad (I)$$

in which:

the symbol $R^1$ represents hydrogen or a monovalent hydrocarbon group selected from linear, branched or cyclic alkyl radicals having from 1 to 25 carbon atoms and linear, branched or cyclic alkoxyalkyl radicals having from 2 to 25 carbon atoms;

the symbols $R^2$, which may be identical or different, correspond to R' and each represent a linear, branched or cyclic alkyl radical having from 1 to 25 carbon atoms; an aryl radical having from 6 to 18 carbon atoms; an arylalkyl radical or an alkylaryl radical ($C_6$-$C_{18}$ aryl, $C_1$-$C_6$ alkyl); $R^2$ optionally bearing at least one halogenated or perhalogenated substituent;

the symbol Y represents either —B—$Y^1$ or $Y^2$:

with $Y^1$ corresponding to:

i.1) a halogen atom (symbol Hal);

ii.1) an $R^3$ group corresponding to a linear, branched or cyclic alkyl radical having from 1 to 8 carbon atoms, an aryl radical having from 6 to 18 carbon atoms, an arylalkyl radical or an alkylaryl radical ($C_6$-$C_{18}$ aryl, $C_1$-$C_6$ alkyl), $R^3$ optionally comprising at least one heteroatom and optionally bearing at least one halogenated or perhalogenated substituent; or iii.1) a monovalent organic functional group W selected from the group consisting of linear, branched or cyclic alkoxyl or acyl radicals having from 2 to 8 carbon atoms, amino, mercapto, cyano, thiocyanato, oxycyanato and (organosilyl)organopolythio groups, with the proviso that these groups may also be substituents of the alkoxyl or acyl radicals, and the mixtures of these radicals and groups;

with $Y^2$ corresponding to R' and representing a monovalent organic functional group $R^4$ selected from functional groups comprising at least one site of ethylenic and/or acetylenic unsaturation selected from:

linear, branched or cyclic alkenyl groups $R^{4.1}$ having from 2 to 10 carbon atoms, linear, branched or cyclic alkynyl groups $R^{4.2}$ having from 2 to 10 carbon atoms, linear, branched or cyclic -(alkenyl-alkynyl) or -(alkynyl-alkenyl) groups $R^{4.3}$ having from 5 to 20 carbon atoms; and with B corresponding to a linear, branched or cyclic $C_1$-$C_{10}$ alkylene residue or a divalent aromatic residue selected from:

(ortho-, meta- or para-)phenylene-(linear or branched $C_2$-$C_6$)alkylene-, (linear or branched $C_2$-$C_6$)alkylene-(ortho-, meta- or para-)phenylene-, and (linear or branched $C_2$-$C_6$)alkylene-(ortho-, meta- or para-)phenylene-(linear or branched $C_2$-$C_6$)alkylene-; and Y optionally comprising at least one heteroatom and/or bearing one or more aromatic groups;

said process consisting essentially of reacting at least one organometallic reactant, which comprises the metal M and which is optionally generated in situ, with at least one organoalkoxysilane (II) selected from di-, tri- and tetraalkoxysilanes and mixtures thereof, in which at least one of the by-products comprises at least one metal alkoxide halide (IV) comprising the metal M, and wherein the alkoxysilane bearing alkoxy functional group(s) of formula OR is an organoalkoxysilane (II) selected from di-, tri- and tetraalkoxysilanes and mixtures thereof and is contacted with the organometallic compound (III) of formula R'M to generate the by-product (IV) comprising at least one metal alkoxide of formula $(X)_x$MOR.

10. The process as defined by claim 9, comprising reacting at least one halogenated organoalkoxysilane (II) selected from the group consisting of di-, tri- and tetraalkoxysilanes and mixtures thereof with at least one organometallic compound (III) of formula $R^2$-M in the presence of at least one solvent (S1) having a starting boiling point SBP(S1) of less than or equal to the boiling point BP(I) of the organomonoalkoxysilane (I) and optionally of at least one solvent (S2) having a starting boiling point SBP(S2) of greater than or equal to SBP(I), SBP(S1) being less than or equal to SBP(S2), said organometallic compound (III) being suited for replacing the alkoxy radicals by organic radicals, according to the following reaction scheme:

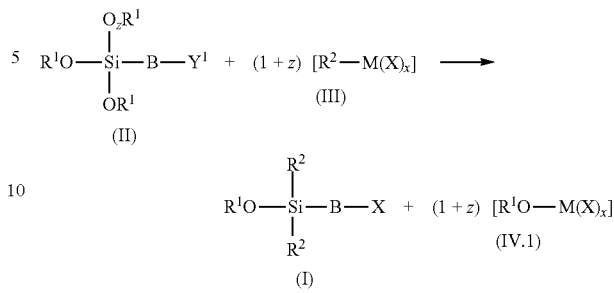

Reaction 3 wherein:

z=0 or 1; and the by-product (IV.1) being a metal alkoxide halide comprising the metal M.

11. The process as defined by claim 10, comprising the following stages:

Phase -a-: addition/reaction comprising the following successive or non-successive stages:

-a1- adding a solution of the organometallic compound (III) in a solvent S1 to the compound (II);

-a2- reacting (II) with (III), and producing a suspension of the reaction products (I) and (IV) in S1;

-a3- optionally adding a solvent S2 before and/or during and/or after reaction -a2-;

Phase -b-: treating the metal alkoxide halide by-product (IV.1) with the agent (A) to obtain the by-products (V.1) and (VI.1);

Phase -c-: removing S1;

Phase -d-:

-d1- dissolving the by-product (V.1), which can be a metal salt (Va.1), in water to obtain a solution;

-d2- optionally removing the solution obtained in d1;

Phase -e-: separating and collecting the organomonoalkoxysilane (I) by distillation;

the product (VI.1) of reactions 1 and 2 included in the distillation residue optionally being recycled in reaction 3;

Phase -f-: optionally hydrolyzing organomonoalkoxysilane (I) into organomonohydroxysilane (I);

with the proviso that the phases -d- and -e- may optionally be inverted.

12. The process as defined by claim 9, comprising reacting at least one non-halogenated organoalkoxysilane (II), selected from the group consisting of di-, tri- and tetraalkoxysilanes and mixtures thereof, with at least one halogenated organic compound (III) in the presence of at least one metal (M) and in the presence of at least one solvent (S1) having a starting boiling point SBP(S1) of less than or equal to the boiling point BP(I) of the organomonoalkoxysilane (I) and optionally of at least one solvent (S2) having a starting boiling point SBP(S2) of greater than or equal to SBP(I), SBP(S1) being less than or equal to SBP(S2), said halogenated organic compound (III) being suited for replacing the alkoxy radicals with organic radicals, according to the following reaction scheme (reaction II/III) where the organoalkoxysilane (II) is a dialkoxysilane:

Reaction 4

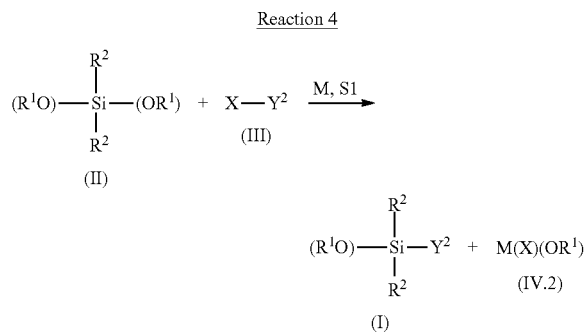

wherein:
the by-product (IV.2) being a metal alkoxide halide comprising the metal M.

13. The process as defined by claim 12, comprising the following stages:
- -a- bringing the metal M and the solvent S1, optionally a solvent S2, together;
- -b- optional activating the reaction by addition of a catalytic amount of at least one halogen and/or of an alkyl halide and/or by heating the reaction medium and/or the metal M;
- -c- adding the organoalkoxysilane (II);
- -d- adding the halogenated organic compound (III), gradually and at a rate of introduction into the reaction medium which is less than or equal to the rate of consumption of (III) in reaction (II/III);
- -e- reacting (II/III) to produce the reaction product (I);
- maintaining the temperature of the reaction medium at a temperature RT of less than or equal to the boiling point BP(S1) of the solvent S1;
- -e1- optionally adding S2;
- -f- treating the by-product (IV.2) with the agent (A) to obtain the co-products (V.2) and (VI.2);
- -h- separating and collecting the organomonoalkoxysilanes (I) and (VI.2) by distillation;
- -i- dissolving in water the by-product (V.2), which can be a metal salt (Va.2);
- -j- optionally removing the solution obtained in -i-;
- -k- removing S1 by distillation;
- -l- optionally hydrolyzing organomonoalkoxysilane (I) into organomonohydroxysilane (I).

14. The process as defined by claim 8, wherein the $Z^2$ radical of the agent (A.b) is selected such that the product (Vb) of reaction 2 has a starting boiling point SBP(Vb) which exhibits, with respect to SBP(S2) and/or with respect to SBP (I), a difference of at least 5° C.

15. The process as defined by claim 10, wherein S1 is selected from the group consisting of the ethereal organic compounds and/or from the group of the acetals and from the subgroup including tetrahydrofuran (THF), methyl-THF (Me-THF), dialkyl ethers, dioxanes and mixtures thereof.

16. The process as defined by claim 10, wherein S2 is selected from the group of the compounds having a starting boiling point SBP defined as follows: 150° C. ≦SBP, and selected from the group consisting of silanes, hydrocarbons, hydrocarbon fractions, (poly)aromatic compounds, alkanes, (poly)ethers, phosphorus-comprising compounds, sulfolanes, ionic liquids, dialkylnitriles and mixtures thereof.

17. The process as defined by claim 9, wherein:
the $R^1$ radicals are selected from the group consisting of the following radicals: methyl, ethyl, n-propyl, isopropyl, n-butyl, $CH_3OCH_2-$, $CH_3OCH_2CH_2-$ and $CH_3OCH(CH_3)CH_2-$,
the $R^2$ radicals are selected from the group consisting of the following radicals: methyl, ethyl, n-propyl, isopropyl, n-butyl, n-hexyl and phenyl,
the $Y^2$ radical represents:

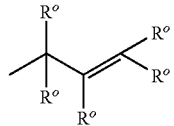

the symbol $R^o$ representing radicals, which may be identical or different, and which correspond to hydrogen or to a linear, branched or cyclic alkyl having from 1 to 8 carbon atoms.

* * * * *